United States Patent
Boël et al.

(10) Patent No.: US 6,465,184 B1
(45) Date of Patent: *Oct. 15, 2002

(54) **ISOLATED NUCLEIC ACID MOLECULE ENCODING PEPTIDES WHICH FORM COMPLEXES WITH MHC MOLECULES HLA-CW*1601 AND USES THEREOF**

(75) Inventors: Pascale Boël; Claude Wildmann; Thierry Boon-Falleur; Pierre van der Bruggen; Pierre Coulie; Jean-Christophe Renauld, all of Brussels (BE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/435,524

(22) Filed: Nov. 8, 1999

Related U.S. Application Data

(60) Division of application No. 09/038,328, filed on Mar. 11, 1998, now Pat. No. 6,110,694, which is a division of application No. 08/573,186, filed on Dec. 15, 1995, now Pat. No. 6,093,540, which is a division of application No. 08/389,360, filed on Feb. 16, 1995, now Pat. No. 5,877,017, which is a continuation-in-part of application No. 08/196,630, filed on Feb. 15, 1994, now Pat. No. 5,683,886, which is a continuation-in-part of application No. 08/079,110, filed on Jun. 17, 1993, now Pat. No. 5,571,711.

(51) Int. Cl.$^7$ .......................... C12Q 1/68; G01N 33/53; G01N 33/574; C12P 19/34; C07H 21/02; A61K 38/00

(52) U.S. Cl. ............... 435/6; 435/7.1; 435/7.2; 435/7.23; 435/91.2; 536/23.1; 530/300

(58) Field of Search ............... 930/10; 435/7.1, 435/7.2, 7.23, 91.2; 536/23.1, 24.2, 24.3, 24.31, 24.33; 530/300, 324

(56) References Cited

U.S. PATENT DOCUMENTS 6,093,540 A * 7/2000 Van Der Bruggen et al. ... 435/6

OTHER PUBLICATIONS

Sequence Homology Search.*

Van der Bruggen et al. A gene encoding an antigen recognized by cytolytic T lymphocytes on a human melanoma. Science, vol. 254, pp. 1643–1647, 1991.*

* cited by examiner

Primary Examiner—John S. Brusca
Assistant Examiner—Young Kim
(74) Attorney, Agent, or Firm—Fulbright & Jaworski LLP.

(57) ABSTRACT

A family of tumor rejection antigen precursors, and the nucleic acid molecules which code for them, are disclosed. These tumor rejection antigen precursors are referred to as BAGE tumor rejection antigen precursors, and the nucleic acid molecules which code for them are referred to as BAGE coding molecules. Various diagnostic and therapeutic uses of the coding sequences and the tumor rejection antigen precursor molecules are described.

7 Claims, 8 Drawing Sheets

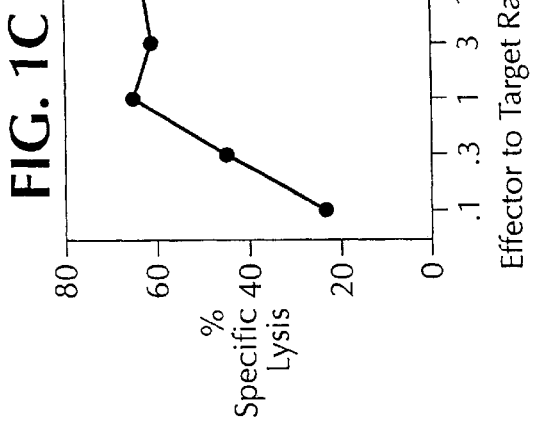
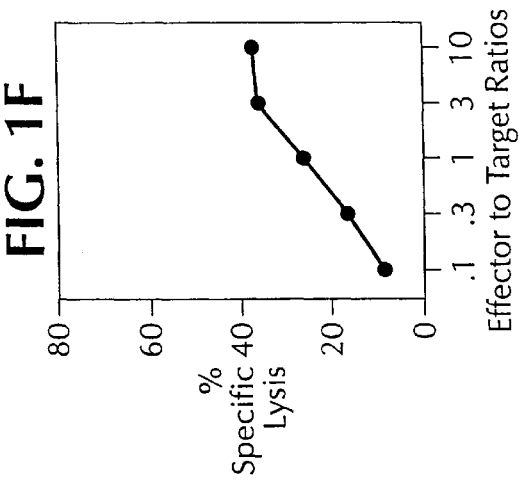
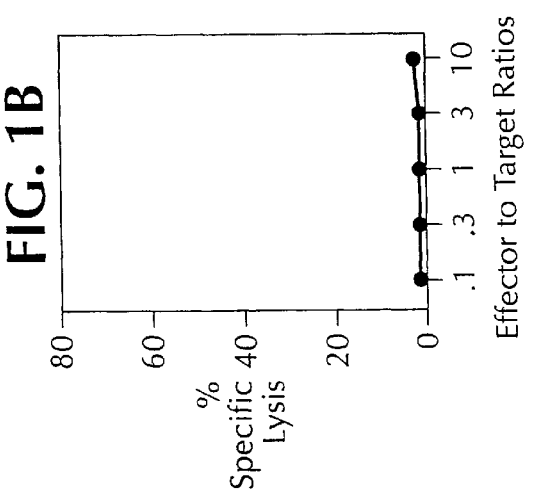
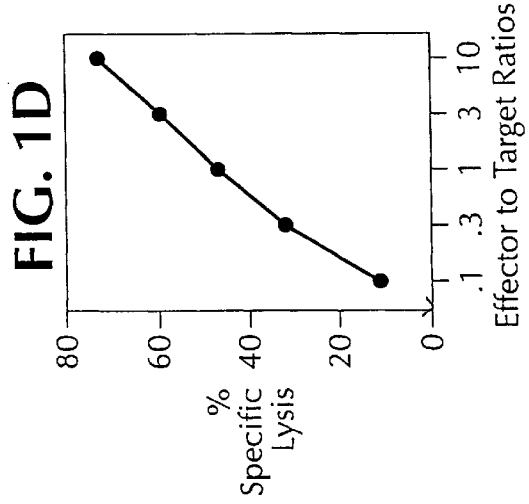
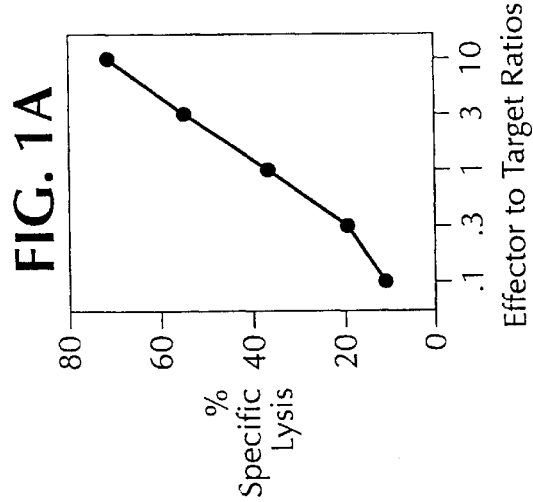

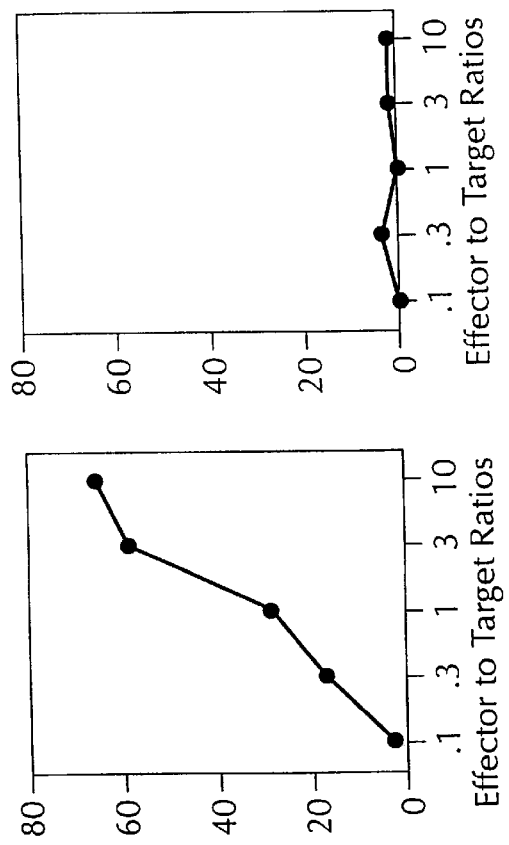

FIG. 4

```
CGCCAATTTA GGGTCTCCGG TATCTCCCGG TGAGCTGCTC TGTTCCCGGC TTAGAGGACC    60

AGGAGAAGGG GGAGCTGGAG GCTGGAGCCT GTAACACCGT GGCTCGTCTC ACTCTGGATG   120
                                                      →
GTGGTGGCAA CAGAGATGGC AGCGCAGCTG GAGTGTTAGG AGGGCGGCCT GAGCGGTAGG   180
                              M  A  A  R  A  V  F | L  A  L|         13

AGTGGGGCTG GAGCAGTAAG ATGGCGGCCA GAGCGGTTTT TCTGGCATTG TCTGCCCAGC   240
 L  L  Q  A  R  L  M  K  E  E  S  P  V  V  S  W  R  S  A  Q         33

TGCTCCAAGC CAGGCTGATG AAGGAGAGT CCCCTGTGGT GAGCTGGAGG TTGGAGCCTG    300
 E  D  G  T  A  L  C  F  I  F                         L  E  P        43

AAGACGGCAC AGCTCTGTGC TTCATCTTCT GAGGTTGTGG CAGCCACGGT GATGGAGACG   360

GCAGCTCAAC AGGAGCAATA GGAGGAGATG GAGTTTCACT GTGTCAGCCA GGATGGTCTC   420

GATCTCCTGA CCTCGTGATC CGCCCGCCTT GGCCTTCCAA AGTGCCGAGA TTACAGCGAT   480

GTGCATTTTG TAAGCACTTT GGAGCCACTA TCAAATGCTG TGAAGAGAAA TGTACCCAGA   540

TGTATCATTA TCCTTGTGCT GCAGGAGCCG GCTCCTTTCA GGATTTCAGT CACATCTTCC   600

TGCTTTGTCC AGAACACATT GACCAAGCTC CTGAAAGATG TAAGTTTACT ACGCATAGAC   660

TTTTAAACTT CAACCAATGT ATTTACTGAA AATAACAAAT GTTGTAAATT CCCTGAGTGT   730

TATTCTACTT GTATTAAAAG GTAATAATAC ATAATCATTA AAATCTGAGG GATCATTGCC   780

AGAGATTGTT GGGGAGGGAA ATGTTATCAA CGGTTTCATT GAAATTAAAT CCAAAAAGTT   840

ATTTCCTCAG AAAAATCAAA TAAAGTTTGC ATGTTTTTTA TTCTTAAAAC ATTTTAAAAA   900

CCACTGTAGA ATGATGTAAA TAGGGACTGT GCAGTATTTC TGACATATAC TATAAAATTA   960

TTAAAAAGTC AATCAGTATT CAACATCTTT TACACTAAAA AGCC                   1004
```

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 1004
      (B) TYPE: nucleic acid
      (C) STRANDEDNESS: single
      (D) TOPOLOGY: linear (xi) SEQUENCE DESCRIPTION: SEQ ID NO: 1:

-continued

```
CGCCAATTTA GGGTCTCCGG TATCTCCCGC TGAGCTGCTC TGTTCCCGGC TTAGAGGACC     60

AGGAGAAGGG GGAGCTGGAG GCTGGAGCCT GTAACACCGT GGCTCGTCTC ACTCTGGATG    120

GTGGTGGCAA CAGAGATGGC AGCGCAGCTG GAGTGTTAGG AGGGCGGCCT GAGCGGTAGG    180

AGTGGGGCTG GAGCAGTAAG ATG GCG GCC AGA GCG GTT TTT CTG GCA TTG TCT   233
                     Met Ala Ala Arg Ala Val Phe Leu Ala Leu Ser
                                   5                          10

GCC CAG CTG CTC CAA GCC AGG CTG ATG AAG GAG GAG TCC CCT GTG GTG     281
Ala Gln Leu Leu Gln Ala Arg Leu Met Lys Glu Glu Ser Pro Val Val
            15                  20                  25

AGC TGG AGG TTG GAG CCT GAA GAC GGC ACA GCT CTG TGC TTC ATC TTC     329
Ser Trp Arg Leu Glu Pro Glu Asp Gly Thr Ala Leu Cys Phe Ile Phe
        30                  35                  40

TGAGGTTGTG GCAGCCACGG TGATGGAGAC GGCAGCTCAA CAGGAGCAAT AGGAGGAGAT    389

GGAGTTTCAC TGTGTCAGCC AGGATGGTCT CGATCTCCTG ACCTCGTGAT CCGCCCGCCT    449

TGGCCTTCCA AAGTGCCGAG ATTACAGCGA TGTGCATTTT GTAAGCACTT GGAGCCACT     509

ATCAAATGCT GTGAAGAGAA ATGTACCCAG ATGTATCATT ATCCTTGTGC TGCAGGAGCC    569

GGCTCCTTTC AGGATTTCAG TCACATCTTC CTGCTTTGTC CAGAACACAT TGACCAAGCT    629

CCTGAAAGAT GTAAGTTTAC TACGCATAGA CTTTTAAACT TCAACCAATG TATTTACTGA    689

AAATAACAAA TGTTGTAAAT TCCCTGAGTG TTATTCTACT TGTATTAAAA GGTAATAATA    749

CATAATCATT AAAATCTGAG GGATCATTGC CAGAGATTGT TGGGGAGGGA AATGTTATCA    809

ACGGTTTCAT TGAAATTAAA TCCAAAAAGT TATTTCCTCA GAAAAATCAA ATAAAGTTTG    869

CATGTTTTTT ATTCTTAAAA CATTTTAAAA ACCACTGTAG AATGATGTAA ATAGGGACTG    929

TGCAGTATTT CTGACATATA CTATAAAATT ATTAAAAAGT CAATCAGTAT TCAACATCTT    989

TTACACTAAA AAGCC                                                    1004
```

(2) INFORMATION FOR SEQ ID NO: 2:

(i) SEQUENCE CHARACTERISTICS:
        (A) LENGTH: 43
        (B) TYPE: amino acid
        (C) STRANDEDNESS: single
        (D) TOPOLOGY: linear (xi) SEQUENCE DESCRIPTION: SEQ ID NO: 2:

```
Met Ala Ala Arg Ala Val Phe Leu Ala Leu Ser Ala Gln Leu Leu Gln
                5                  10                  15

Ala Arg Leu Met Lys Glu Glu Ser Pro Val Val Ser Trp Arg Leu Glu
            20                  25                  30

Pro Glu Asp Gly Thr Ala Leu Cys Phe Ile Phe
        35                  40
```

(2) INFORMATION FOR SEQ ID NO: 3:

(i) SEQUENCE CHARACTERISTICS:
        (A) LENGTH: 9
        (B) TYPE: amino acid
        (C) STRANDEDNESS: single
        (D) TOPOLOGY: linear (xi) SEQUENCE DESCRIPTION: SEQ ID NO: 3:

```
Ala Ala Arg Ala Val Phe Leu Ala Leu
                5
```

(2) INFORMATION FOR SEQ ID NO: 4:

(i) SEQUENCE CHARACTERISTICS:
                (A) LENGTH: 9
                (B) TYPE: amino acid
                (C) STRANDEDNESS: single
                (D) TOPOLOGY: linear (xi) SEQUENCE DESCRIPTION: SEQ ID NO: 4:

Ala Arg Ala Val Phe Leu Ala Leu Phe
              5

(2) INFORMATION FOR SEQ ID NO: 5

(i) SEQUENCE CHARACTERISTICS:
                (A) LENGTH: 9
                (B) TYPE: amino acid
                (C) STRANDEDNESS: single
                (D) TOPOLOGY: linear (xi) SEQUENCE DESCRIPTION: SEQ ID NO: 5:

Met Ala Ala Arg Ala Val Phe Leu Ala
              5

(2) INFORMATION FOR SEQ ID NO: 6:

(i) SEQUENCE CHARACTERISTICS:
                (A) LENGTH: 18
                (B) TYPE: nucleic acid
                (C) STRANDEDNESS: single
                (D) TOPOLOGY: linear (xi) SEQUENCE DESCRIPTION: SEQ ID NO: 6:

TGGCTCGTCT CACTCTGG                                                     18

(2) INFORMATION FOR SEQ ID NO: 7:

(i) SEQUENCE CHARACTERISTICS:
                (A) LENGTH: 19
                (B) TYPE: nucleic acid
                (C) STRANDEDNESS: single
                (D) TOPOLOGY: linear (xi) SEQUENCE DESCRIPTION: SEQ ID NO: 7:

CCTCCTATTG CTCCTGTTG                                                    19

(2) INFORMATION FOR SEQ ID NO: 8:

(i) SEQUENCE CHARACTERISTICS:
                (A) LENGTH: 19
                (B) TYPE: nucleic acid
                (C) STRANDEDNESS: single
                (D) TOPOLOGY: linear (xi) SEQUENCE DESCRIPTION: SEQ ID NO: 8:

GGCATCGTGA TGGACTCCG                                                    19

(2) INFORMATION FOR SEQ ID NO: 9:

(i) SEQUENCE CHARACTERISTICS:
                (A) LENGTH: 19
                (B) TYPE: nucleic acid
                (C) STRANDEDNESS: single
                (D) TOPOLOGY: linear (xi) SEQUENCE DESCRIPTION: SEQ ID NO: 9:

GCTGGAAGGT GGACAGCGA                                                    19

US 6,465,184 B1

ISOLATED NUCLEIC ACID MOLECULE ENCODING PEPTIDES WHICH FORM COMPLEXES WITH MHC MOLECULES HLA-CW*1601 AND USES THEREOF

CROSS REFERENCE TO RELATED APPLICATIONS

This application is a divisional of application Ser. No. 09/038,328 filed on Mar. 11, 1998, now U.S. Pat. No. 6,110,694, which is a divisional of application Ser. No. 08/573,186 filed on Dec. 15, 1995, now U.S. Pat. No. 6,093,540 which is a divisional of application Ser. No. 08/389,360 filed on Feb. 16, 1995 (now U.S. Pat. No. 5,877,017), which is a continuation-in-part of application Ser. No. 08/196,630 filed Feb. 15, 1994 (now U.S. Pat. No. 5,683,886) which is a continuation-in-part of application Ser. No. 08/079,110 filed Jun. 17, 1993, now U.S. Pat. No. 5,571,711. All related applications and patents cited are herein incorporated by reference.

FIELD OF THE INVENTION

This invention relates to nucleic acid molecules, proteins, and peptides which are useful in connection with the diagnosis and treatment of pathological conditions. This invention further relates to said proteins and peptides, which are processed to a peptide presented by the MHC molecule HLA-Cw*1601, and the presented peptide itself. These peptides are useful in diagnosis and therapeutic contexts.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See Male et al., *Advanced Immunology* (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See Barinaga, *Science*, 257: 880 (1992); Fremont et al., *Science*, 257: 919 (1992); Matsumura et al., *Science*, 257: 927 (1992); and Latron et al., *Science*, 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., *Immunogenetics*, 35: 145 (1992); van der Bruggen et al., *Science*, 254: 1643 (1991), for further information on this family of genes. Also, see U.S. Pat. No. 5,342,774.

In U.S. patent application Ser. No. 938,334, now U.S. Pat. No. 5,405,940 the disclosure of which is incorporated by reference, nonapeptides are taught which are presented by the HLA-A1 molecule. The reference teaches that given the known specificity of particular peptides for particular HLA molecules, a particular peptide is expected to bind one HLA molecule, but not others. This is important, because different individuals possess different HLA phenotypes. As a result, while identification of a particular peptide as being a partner for a specific HLA molecule has diagnostic and therapeutic ramifications, these are, only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 now U.S. Pat. No. 5,629,166 and incorporated herein by reference, it is disclosed that the MAGE-1 expression product is processed to a second TRA. This second TRA is presented by HLA-Cw*1601 molecule. The disclosure shows that a given TRAP can yield a plurality of TRAs.

In U.S. patent application Ser. No. 994,928, filed Dec. 22, 1992, and incorporated by reference herein now abandoned, tyrosinase is described as a tumor rejection antigen precursor. This reference discloses that a molecule which is produced by some normal cells (e.g., melanocytes), is processed in tumor cells to yield a tumor rejection antigen that is presented by HLA-A2 molecules.

In U.S. patent application Ser. No. 08/032,978, filed Mar. 18, 1993, now U.S. Pat. No. 5,620,886 and incorporated herein by reference, a second TRA, not derived from tyrosinase, is taught to be presented by HLA-A2 molecules. The TRA is derived from a TRAP, but is coded for by a non MAGE gene. This disclosure shows that a particular HLA molecule may present TRAs derived from different sources.

In U.S. patent application Ser. No. 08/079,110 filed Jun. 17, 1993, now U.S. Pat. No. 5,571,711 which is incorporated herein by reference, a new family of genes, referred to therein as the BAGE family, is disclosed. It was observed that these genes also code for tumor rejection antigen precursors. It is disclosed in the application that the MHC molecule known as HLA-Cw*1601 presents a tumor rejection antigen derived from a BAGE tumor rejection antigen precursor; however, the tumor rejection antigen was not disclosed. The tumor rejection antigen is disclosed in U.S. patent application Ser. No. 08/196,630 filed Feb. 15, 1994, now U.S. Pat. No. 5,683,886 which is incorporated herein by reference. The application also discloses ramifications stemming from the tumor rejection antigen, as well as therapeutic and diagnostic methods utilizing the antigen.

The present application is directed to isolated nucleic acid molecules which encode BAGE tumor rejection antigen precursors described in patent application Ser. No. 08/196,630 now U.S. Pat. No. 5,683,886. The present application is further directed to therapeutic and diagnostic methods utilizing the isolated BAGE nucleic acid molecule.

The invention is elaborated upon further in the disclosure which follows.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 1 is comprised of FIG. 1A through FIG. 1F. These show lytic activity of CTL clone 82/82 on MZ2-MEL sublines, MZ2-MEL.3.0, MZ2-MEL.3.1 and MZ2-MEL.B.TC.4, lytic activity of CTL clone 82/82 on MZ2-MEL subline MZ2-MEL.43 and on melanoma cell lines MI4024/1-MEL and LB17-MEL, which were derived from HLA-Cw*1601 positive patients.

FIG. 3 is comprised of FIG. 3A through FIG. 3D. These show lysis by CTL clone 82/82 of P1.HTR mouse cells cotransfected with expression vectors carrying HLA-Cw*1601 and cDNA-AD5, as well as untransfected P1.HTR, and P1.HTR transfected with HLA-Cw*1601 alone, as well as lysis by CTL clone 82/82 of P1.HTR transfected with HLA-Cw*1601 and BAGE-derived nonapeptide AARAVFLAL; (SEQ ID NO: 3).

FIG. 4 sets forth nucleotide (SEQ ID NO:1) and amino acid sequences (SEQ ID NO: 2) of a BAGE tumor rejection antigen precursor. The boxed segment is a tumor rejection antigen derived from the precursor;

DETAILED DESCRIPTION OF THE INVENTION

EXAMPLE 1

Figure 2:
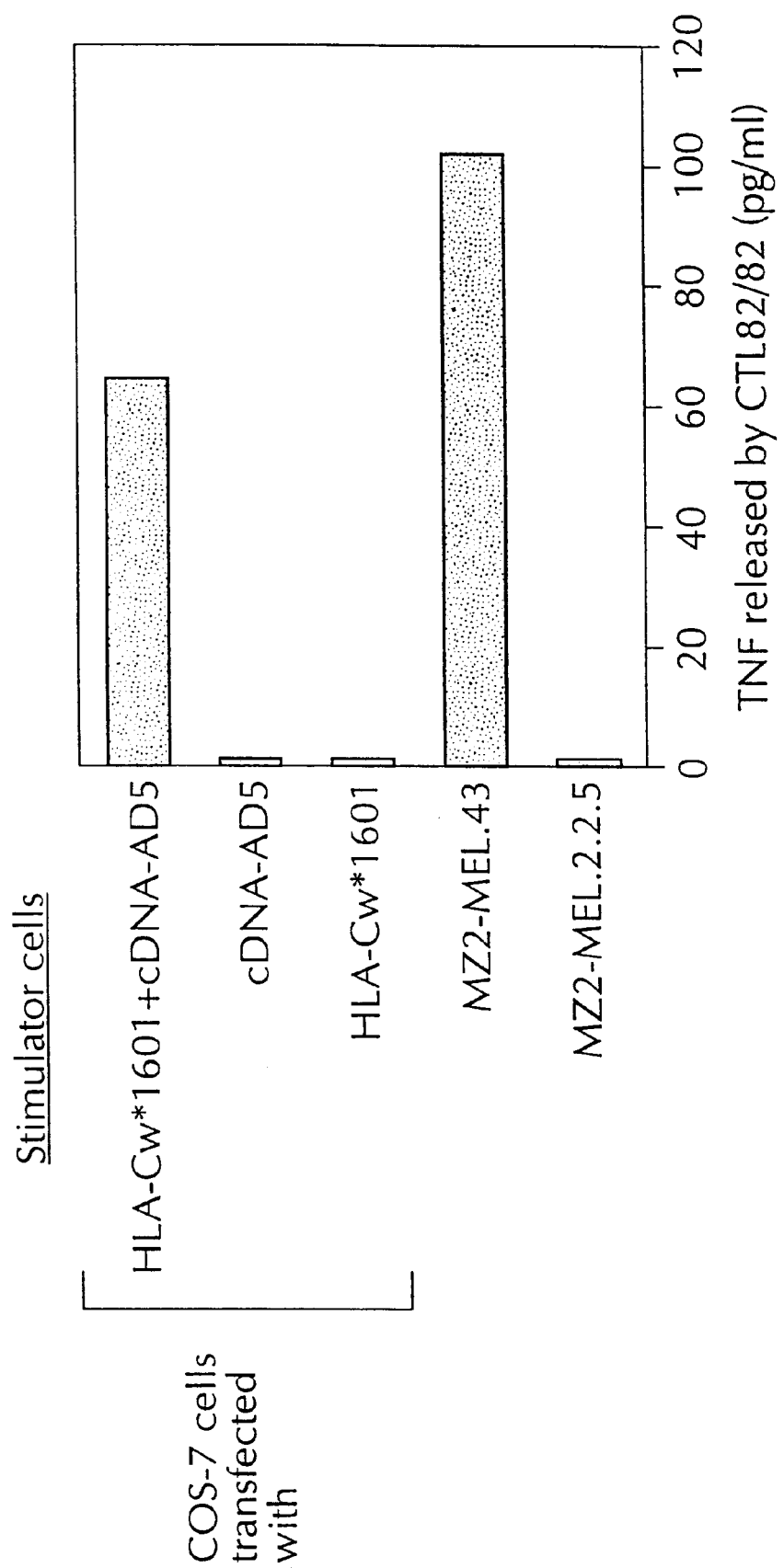
FIG. 2 shows TNF release by CTL 82/82 when put into contact with COS-7 cells transfected with HLA-Cw*1601 alone, in combination with cDNA-AD5, or transfected with AD5 alone. CTL 82/82 was also put into contact with MZ2-MEL.43 and MZ2-MEL.2.2.5, as controls.

Melanoma cell line MZ2-MEL was derived from patient MZ2 using standard methodologies. This cell line is described in PCT Application PCT/US92/04354, filed May 22, 1992, published Nov. 26, 1992, which is incorporated herein by reference. Once the cell line was established, a sample of it was irradiated, so as to render it non-proliferative. A number of subclones were obtained from MZ2-MEL. Specifically, clonal line MZ2-MEL.3.0 was obtained from MZ2-MEL by limiting dilution. The MZ2-MEL.3.0 culture was then cultured further. After more than 150 generations in culture, a new subline, denoted MZ2-MEL.3.1, was obtained. MZ2-MEL.3.1 was found to be resistant to a large fraction of autologous CTL clones that had strong lytic activity on MZ2-MEL.3.0. It was determined that MZ2-MEL.3.1 had lost the genes coding for HLA-A29, B44, and Cw*1601 (see van der Bruggen et al., Eur. J. Immunol., 24:2134–2140 (1994), which is incorporated herein by reference).

Subline MZ2-MEL.43 was derived by limiting dilution from MZ2-MEL.3.0 cells that has survived mutagen treatment (Van den Eynde et al., Int. J. Cancer, 44:634–640 (1989)). Clonal subline MZ2-MEL.2.2, which does not express antigen MZ2-E, was selected from subclone MZ2-MEL.3.1 with an autologous anti-MZ2-E CTL clone (Van den Eynde et al., supra). Subline MZ2-MEL.2.2.5 was selected from subline MZ2-MEL.2.2 with an anti-MZ2-F CTL clone. MZ2-MEL.B.TC.4 was obtained by transfecting HLA-Cw*1601 gene into subline MZ2-MEL.2.2.5 (van der Bruggen et al., supra). Melanoma cell lines were grown as previously described by Van den Eynde et al., supra and Traversari et al.; Immunogenetics, 35:145–152 (1992).

Cytolytic T cell clones ("CTLs") specific to cell line MZ2-MEL were obtained utilizing irradiated MZ2-MEL cells. Specifically, a sample of peripheral blood mononuclear cells ("PBMCs") was taken from patient MZ2, and contacted to the irradiated melanoma cells. The mixture was observed for lysis of the melanoma cells, which indicated that CTLs specific for a complex of peptide and HLA molecule presented by the melanoma cells were present in the sample.

The lysis assay employed was a chromium release assay following Herin et al., Int. J. Cancer, 39:390–396 (1987), which is incorporated herein by reference. The assay, however, is described herein. The target melanoma cells were grown in vitro, and then resuspended at $4 \times 10^7$ cells/ml in DMEM, supplemented with DMEM with 10 mM HEPES and 50% FCS, and incubated for 60 minutes at 37° C. with 200 $\mu$Ci/ml of Na($^{51}$Cr)O$_4$. Labelled cells were washed three times with DMEM, supplemented with 10 mM HEPES. These were then resuspended in DMEM supplemented with 10 mM HEPES and 10% FCS, after which 100 $\mu$l aliquots containing $10^3$ cells, were distributed into 96 well microplates. Samples of PBLs were added in 100 $\mu$l of the same medium, and assays were carried out in duplicate. Plates were centrifuged for 4 minutes at 100 g, and incubated for four hours at 37° C. in a 8% CO$_2$ atmosphere.

Plates were centrifuged again, and 100 $\mu$l aliquots of supernatant were collected and counted. Percentage of $^{51}$Cr release was calculated as follows:

$$\% \ ^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 $\mu$l of medium alone, and MR is maximum release, obtained by adding 100 $\mu$l 0.3% Triton X-100 to target cells.

Those mononuclear blood samples which showed high CTL activity were expanded and cloned via limiting dilution, and were screened again, using the same methodology. The CTL clone MZ2-CTL 82/82 was thus isolated. The clone is referred to as "82/82" hereafter.

MZ2-MEL sublines and other melanoma lines were put into contact with CTL clone 82/82 and lytic activity was determined by measuring chromium release. Chromium release was measured after 4 hours. FIG. 1A shows lysis of MZ2-MEL.3.0 and MZ2-MEL.B.TC.4. Subline MZ2-MEL.3.1 was not lysed by CTL 82/82. FIG. 1B shows that there is lysis of clonal line MZ2-MEL.43 by CTL 82/82. In addition, melanoma cell lines MI4024/1-MEL and LB17-MEL, which carry the HLA-Cw*1601 allele, were lysed by CTL 82/82.

EXAMPLE 2

The gene which codes for the antigen recognized by CTL 82/82 was identified. As described herein, the gene was identified by cotransfecting HLA-Cw*1601 cDNA with a cDNA library. Due to the specificity of CTL 82/82 for MZ2-MEL.43, the cDNA of this cell line was used to construct the cDNA library. In order to construct the cDNA library from MZ2-MEL.43, poly-A+ RNA was extracted from MZ2-MEL.43 cells using an mRNA extraction kit. The mRNA was converted to cDNA using random primers, ligated to adaptors following standard techniques, and inserted into the EcoRI site of expression vector pcD-SRα, which contains the replication origin of SV40. Recombinant plasmids were electroporated into *E. coli* JM101 and selected with ampicillin (50 μg/ml). The library contained 66,000 inserts and was divided into 87 pools of 400 bacteria and 297 pools of 200 bacteria. Each of these pools comprised approximately 280 or 140 different cDNAs respectively, as about 70% of the plasmids carried an insert. Each pool of bacteria was amplified to saturation and plasmid DNA was extracted by the well known alkaline lysis method.

Plasmid pcD-SRα was transfected with HLA-Cw*1601 cDNA. cDNA pools were then cotransfected with the pcD-SRα plasmid containing HLA-Cw*1601 cDNA into duplicate microcultures of COS-7 cells. Transfection was performed by the DEAE-dextran-chloroquine method (Seed et al., *Proc. Natl. Acad. Sci. USA*, 84:3365–3369 (1987); Brichard et al., *Annal. Biochem.*, 162:156–159 (1993); Coulie et al., *J. Exp. Med.*, 180:35–42 (1994)). Briefly, $1.5 \times 10^4$ COS-7 cells were transfected with 100 ng of plasmid pcD-SRα containing cDNA of HLA-Cw*1601, and 100 ng of a pool of the cDNA library or 100 ng of a cDNA clone. The HLA-Cw*1601 cDNA was isolated from a cDNA library prepared with RNA extracted from subline MZ2-MEL.43 (van der Bruggen et al., supra).

Cotransfectants were tested after 24 or 48 hours for their ability to stimulate the production of tumor necrosis factor (TNF) by CTLs (Traversari et al., *Immunogenetics*, 235:145–152 (1992)). 1500 CTLs were added in 100 μl of Iscove's medium (Gibco BRL) containing 10% human serum and 20 U/ml r-hu-IL-2 to microwells containing target cells. After 24 hours, the supernatant was collected and its TNF content was determined by testing its cytotoxic effect on cells of WEHI-164 clone 13 (Espevik et al., *J. Immunol. Methods*, 95:99–105 (1986)) in an MTT colorimetric assay (Hansen et al., *J. Cancer*, 39:390–396 (1989) and Traversari et al., supra).

Among the 384 pools of cDNAs (297 of 200 bacteria and 87 of 400) that were transfected, two produced positive supernatants containing more than 40 pg/ml of TNF, whereas TNF concentration in all of the microcultures transfected with the other pools was lower than 5 pg/ml. From one of these cDNA pools which contained 400 independent bacteria, 800 bacteria were subcloned. Plasmid DNA was extracted from each of them and transfected into COS-7 cells together with the HLA-Cw*1601 construct described supra. Twelve clones conferred recognition by CTL 82/82. The result obtained with one of them, denoted cDNA-AD5, is represented in FIG. 2.

FIG. 2 shows stimulation of CTL 82/82 by COS-7 cells cotransfected with cDNA-AD5 and with an HLA-Cw*1601 cDNA, or transfected with one of these cDNAs. The cDNAs were inserted in expression vector pcD-SRα as described supra. Samples of CTL 82/82 were added one day after the transfection and the TNF content of the supernatant was estimated one day later by testing its toxicity on cells of WEHI-164 clone 13. Positive and negative controls were developed with MZ2-MEL.43 and MZ2-MEL.2.2.5 cells.

To confirm the results obtained with cDNA-AD5 in transient transfections, stable transfectants were also prepared. P1.HTR, a highly transfectable variant derived from mouse tumor cell line P815 (Van Pel et al., *Som. Cell Genet.*, 11:467–475 (1985)), was transfected with both HLA-Cw*1601 and cDNA-AD5, using the calcium phosphate precipitate method with plasmid pSVtkneoβ conferring resistance to geneticin (Nicolas et al., *CSH Conferences Cell Prolif.*, 10:469–485 (1983)) and HLA-Cw*1601 alone, or both HLA-Cw*1601 and cDNA-AD5. The relevant cDNAs were inserted in expression vector pcD-SRα as described supra. Clonal sublines were isolated from a geneticin-resistant transfected population. Transfected cells, when put into contact with CTL 82/82, were lysed by CTL 82/82, indicating that the antigen can also be processed in these mouse cells. FIG. 3A shows lysis by CTL clone 82/82 of P1.HTR mouse cells cotransfected with expression vectors carrying HLA-Cw*1601 and cDNA-AD5. Untransfected P1.HTR and P1.HTR transfected with HLA-Cw*1601 alone were also tested.

EXAMPLE 3

DNA sequence analysis of cDNA-AD5 was performed by specific priming with synthetic oligonucleotides. SEQ ID NO: 1 presents cDNA nucleotide information for the identified gene, referred to herein as "BAGE". The sequencing reactions were performed by the dideoxy-chain termination method (T7 Sequencing Kit, Pharmacia Uppsala Sweden, ΔTAq™ Cycle-Sequencing Kit, USB, Cleveland, Ohio). The computer search for the sequence homology was done with programs FASTA@EMBL-Heidelberg and blast@ncbi.nlm.nih.gov. The sequence bears no significant similarity to any other sequence presently recorded in databanks, except for an Alu repeat (nucleotides 385 to 484) located outside of the coding region.

EXAMPLE 4

The region of BAGE which codes for the antigen presented by HLA-Cw*1601 was determined. in order to identify this region, a large number of truncated BAGE cDNA clones were produced. By digesting BAGE with exonuclease III for various incubation times, progressive deletions starting from the 3' end were generated. The truncated variants were religated into pcDNAI/Amp, electroporated into *E. coli* strain DH5αF'IQ, and selected via ampicillin (50 μg/ml). 438 clones were obtained in this way.

The plasmid DNA was obtained from these 438 cones, and transfected into COS-7 cells together with HLA-Cw*1601 cDNA to test for their ability to code for the antigen. The transfectants were tested in a TNF release assay, as described supra. Positive clones were those which stimulated TNF release by CTL 82/82.

Once cells were divided into positive and negative transfectants, the sequences of plasmid DNA from 5 positives and 5 negatives were determined. Clone 19C2, a positive clone, contained part of the open reading frame for the BAGE gene described supra, from nucleotide 201 to nucleotide 267. In contrast, clone 17G12, a negative transfectant, contained nucleotides 201–206. This indicated that the antigenic peptide was encoded by the first 67 nucleotides of the open reading frame.

FIG. 4, which shows the sequence of BAGE, also shows a putative protein of 43 amino acids encoded by the largest open reading frame. This protein was identified as containing the sequence of the presented peptide. The 43 amino acid protein, referred to herein as SEQ ID NO: 2, is as follows:

```
Met Ala Ala Arg Ala Val Phe Leu Ala Leu Ser
Ala Gln Leu Leu Gln Ala Arg Leu Met Lys Glu
Glu Ser Pro Val Val Ser Trp Arg Leu Glu Pro
Glu Asp Gly Thr Ala Leu Cys Phe Ile Phe
```

The sequence corresponding to the peptide recognized in association with HLA-Cw*1601 by MZ2-CTL 82/82 is indicated in a box. The sequence is referred to herein as SEQ ID NO: 3: Ala Ala Arg Ala Val Phe Leu Ala Leu. The sequence of primers VDB85 (SEQ ID NO: 6) (sense) and VDB86 (SEQ ID NO: 7) (anti-sense) used for PCR amplification, as discussed in Example 4, are underlined with arrows.

Several synthetic peptides were prepared on this basis. Peptides were synthesized on solid phase using F-moc for transient NH2-terminal protection as described by Atherton et al., *J. Chem. Soc. Lond. Perkin Trans.*, 1:538–546 (1981) and characterized by mass spectrometry. All peptides were >90% pure as indicated by analytical HPLC. Lyophilized peptides were dissolved at 20 mg/ml in DMSO, diluted at 2 mg/ml in 10 mM acetic acid and stored at 80° C. Peptides were tested in a CTL stimulation assay with COS-7 cells transfected by HLA-Cw*1601 and incubated with the peptides. They were also tested by chromium release assay as previously described (Boon et al., *J. Exp. Med.*, 152:1184–1193 (1980)). In this peptide sensitization assay, target cells were $^{51}$Cr-labelled for one hour at 37° C. and washed extensively. 1000 target cells were then incubated in 96-well microplates in the presence of various concentrations of peptide for 30 minutes at 37° C. before CTL 82/82 cells were added. Chromium release was measured after 4 hours at 37° C.

Figure 8:
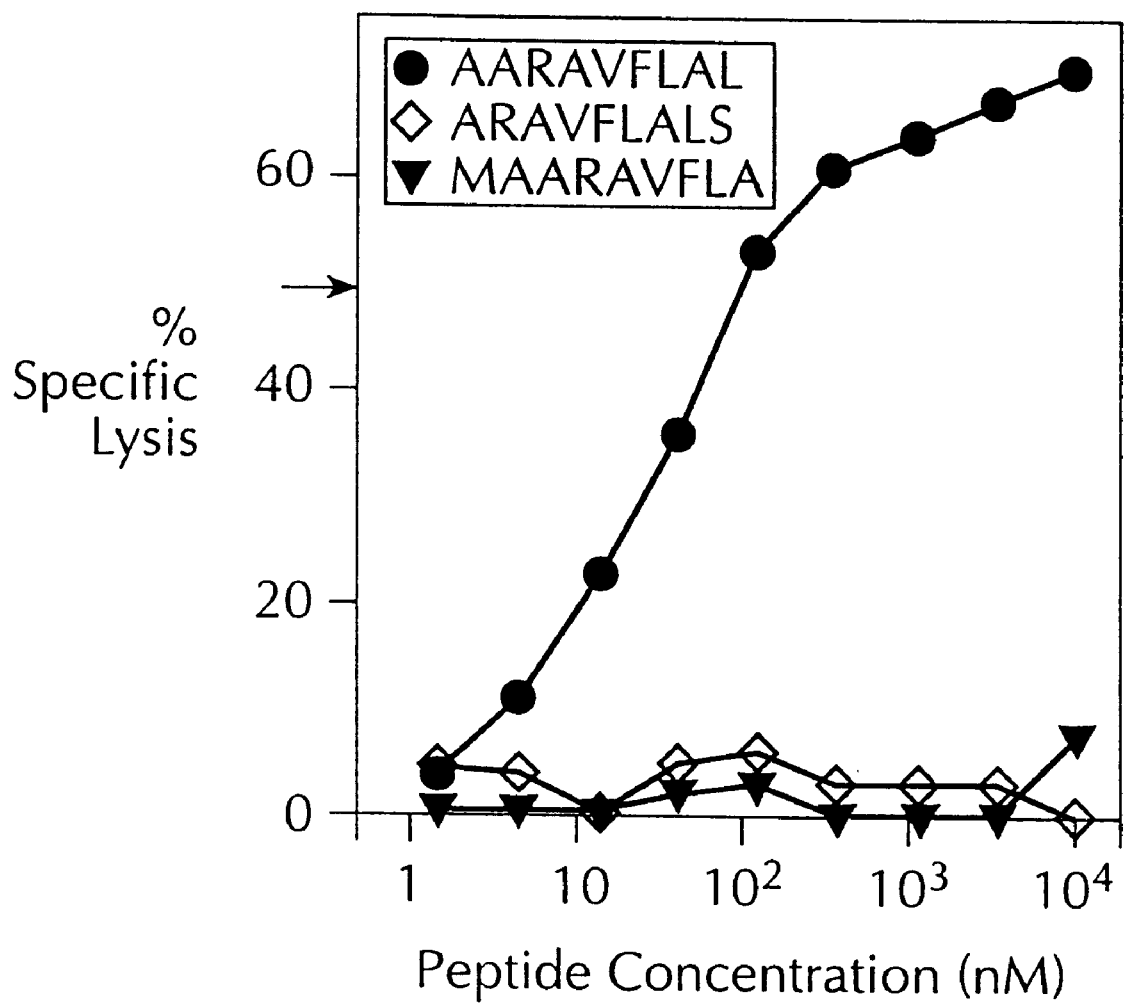
FIG. 8 represents lysis by CTL 82/82 of lymphoblastoid cell line MZ2-EBV incubated with BAGE-encoded peptide AARAVFLAL (SEQ ID NO: 3) or with nonapeptides ARAVFLALF (SEQ ID NO: 4) or MAARAVFLA (SEQ ID NO: 5).

FIG. 8 shows lysis by CTL 82/82 of lymphoblastoid cell line MZ2-EBV incubated with BAGE encoded peptide AARAVFLAL (SEQ ID NO: 3). The final concentration of peptides during the incubation of the target cells with the CTL is indicated. The arrow indicates the percentage of lysis of MZ2-MEL.43 cells. Sensitization of a lymphoblastoid cell line from patient MZ2 to lysis by CTL 82/82 was observed with nonapeptide AARAVFLAL (SEQ ID NO: 3) (amino acids 2–10, FIG. 4) Half-maximal lysis was obtained at a peptide concentration of 30 nM (FIG. 8). Nonapeptides that did not include the N-terminal Ala, or ARAVFLALF (SEQ ID NO: 4) or the C-terminal Leu, MAARAVFLA (SEQ ID NO: 5) were not able to sensitize target cells to lysis. P1.HTR cells were transfected with HLA-Cw*1601 and were incubated with nonapeptide AARAVFLAL (SEQ ID NO: 3). The transfected cells were lysed by CTL 82/82. FIG. 3B shows lysis by CTL clone 82/82 of P1.HTR transfected with HLA-Cw*1601 and incubated with 1 μM of the PAGE-encoded nonapeptide AARAVFLAL (SEQ ID NO: 3). Lysis of chromium-labelled cells was tested after 4 hours.

From two MLTCs set up with different blood samples of patient MZ2, six CTL clones that recognized the BAGE/HLA-Cw*1601 antigen were derived. They produced TNF in the presence of COS-7 cells cotransfected with HLA-Cw*1601 and BAGE cDNA-ADS. They also responded to cells transfected with HLA-Cw*1601 and incubated with nonapeptide AARAVFLAL (SEQ ID NO: 3). It appears that at least 3 different CTL precursors can recognize this BAGE antigen. CTL clone 82/1 expressed. Vα2, Vα3 and Vβ13 while CTL clone 25/244 expressed Vα8 and Vβ8, whereas CTL clone 82/82 expressed Vα3, Vα4 and Vβ13. Vα and Vβ expression were determined as follows: Total RNA from the different CTL clones was prepared by using RNAzol*B (Cinna/Biotecx, Friendswood, Tex.). Single-stranded cDNA synthesis was carried with oligo(dT) and Moloney murine leukemia virus-derived reverse transcriptase without RNAse H activity. PCR was carried out by amplification of TCR-α and -β cDNA with the oligonucleotide primers complementary to TCR variable (Vα1-W29, Vβ1-W24) and constant (Cα, Cβ) region sequences described by Geneveé et al., *Eur. J. Immunol.*, 22:1261–1269 (1992). Specificity of TCR Vα and Vβ PCR amplification was assessed by Southern blotting and hybridization with $^{32}$P-labelled Cα or Cβ oligonucleotides internal to the ones used for amplification.

EXAMPLE 5

The expression of BAGE in tissues was tested by reverse transcription and nested PCR (van der Bruggen et al., supra). cDNAs from melanoma lines, tumor and normal tissue samples, and of genomic DNA from subline MZ2-MEL.43, were amplified by PCR. Total RNA was extracted by the guanidine-isothiocyanate procedure as described by Davis et al., *Basic Methods in Molecular Biology*, pp. 130–135 (New York, Elsevier, 1986). Reverse transcription was performed on 2 βg of total RNA in a reaction volume of 20 μl with 4 βl of 5×reverse transcriptase buffer, 2 μl of a 20 mM solution of oligo(dT) 15 primer, 20 U of RNasin, 2 μl of 0.1 M dithiothreitol and 200 U of MOMLV reverse transcriptase plus 1 μl of each of 10 mM solution of DNTP. The reactants were incubated at 42° C. for 60 minutes. One twentieth of the cDNA product was then supplemented with 5 μl of 10 ×thermostable DNA polymerase buffer, 1 μl each of 10 mM solution of DNTP, 1 μl each of 25 μl solution of primers, 1 U of DynaZyme™ and water to a final volume of 50 μl. The PCR primers were 5'-TGGCTCGTCTCACTCTGG-3' (SEQ ID NO: 6) (VDB85, sense, nucleotide 100 to 117) and 5'-CCTCCTATTGCTCCTGTTG-3' (SEQ ID NO: 7) (VDB86, anti-sense, nucleotide 367 to 385). PCR was performed for 30 cycles (1 minute at 94° C., 2 minutes at 62° C. and 2 minutes at 73° C.). 10 μl of the PCR product was size-fractionated on a 1.5% agarose gel. The quality of RNA preparations was tested by PCR amplification of human β-actin cDNA with primers 5'-GGCATCGTGATGGACTCCG-3' (SEQ ID NO: 8) (exon 4, sense) and 5'-GCTGGAAGGTGGACAGCGA-3' (SEQ ID NO: 9) (exon 6, anti-sense) for 21 cycles of 1 minute at 94° C., 2 minutes at 68° C. and 2 minutes at 72° C. by AmpliTaq DNA polymerase.

Figure 7:
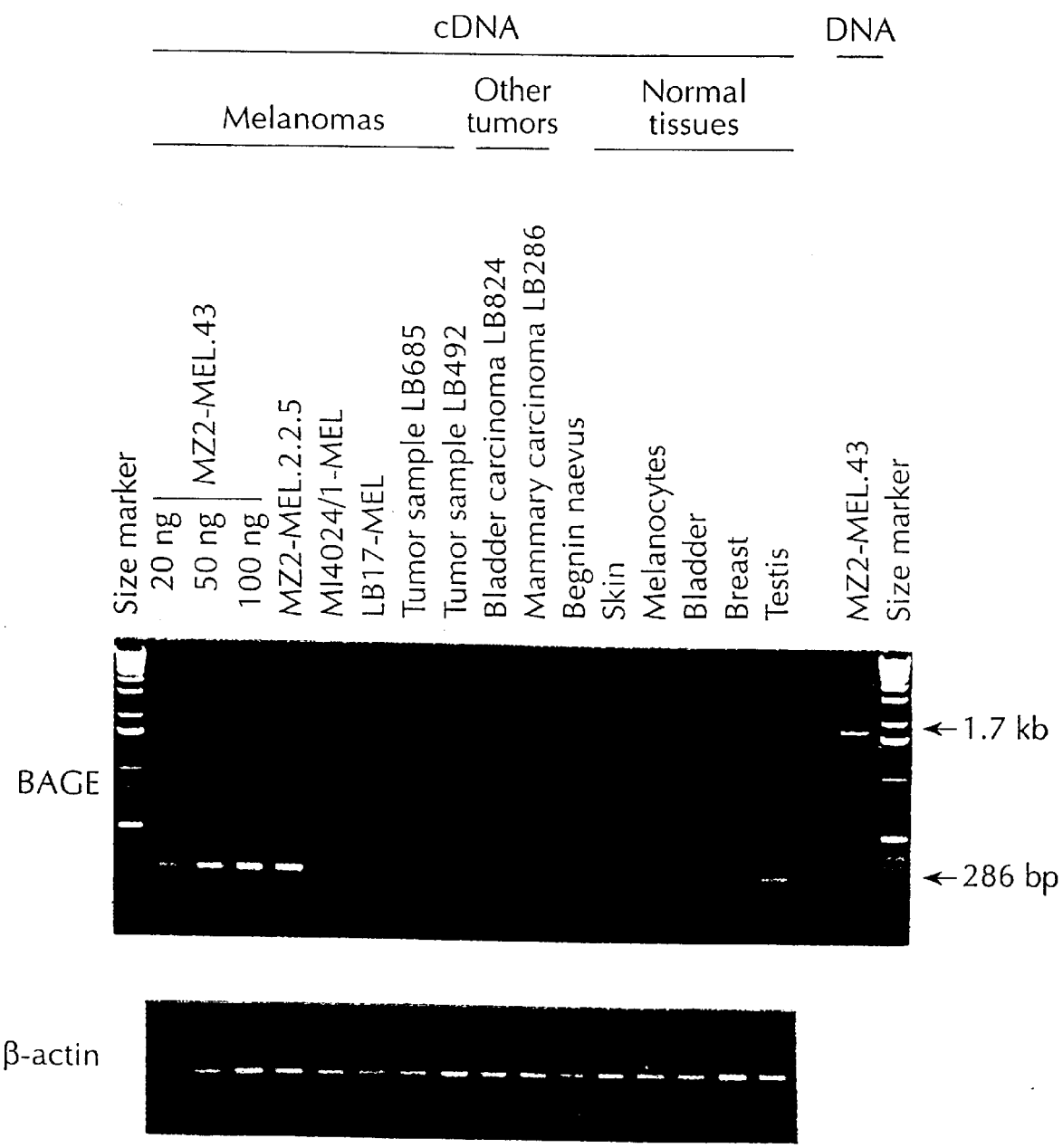
FIG. 7 represents PCR amplification of cDNAs from melanoma lines, tumor and normal samples, and of genomic DNA from subline MZ2-MEL.43.

PCR products were visualized on a 1.5% agarose gel stained with ethidium bromide. No expression of gene BAGE was found in normal adult tissues except in testis (see FIG. 7 and Table 1, below). The gene was also silent in placenta and umbilical cord and in several tissue samples from fetuses older than 20 weeks. No expression of BAGE was found in the twelve EBV-transformed lymphoblastoid cell lines tested nor in blood lymphocytes stimulated with phytohemagglutinin.

TABLE 1

Expression of Gene BAGE by Normal Adult and Fetal Tissue

|  | expression |
|---|---|
| Adult tissues | |
| Adrenal gland | – |
| Bone marrow | – |
| Brain | – |
| Breast | – |
| Cerebellum | – |

TABLE 1-continued

Expression of Gene BAGE by Normal Adult and Fetal Tissue

|  | expression |
|---|---|
| Colon | − |
| Heart | − |
| Kidney | − |
| Liver | − |
| Lung | − |
| Melanocytes | − |
| Muscle | − |
| Ovary | − |
| Prostate | − |
| Skin | − |
| Sperm | − |
| Splenocytes | − |
| Stomach | − |
| Testis | + |
| Thymocytes | − |
| Urinary bladder | − |
| Uterus | − |
| Placenta | − |
| Umbilical cord | − |
| Benign naevus | − |
| Fetal tissues | |
| Fibroblasts | − |
| Brain | − |
| Liver | − |
| Spleen | − |
| Thymus | − |
| Testis | − |

BAGE appears to be silent in normal adult tissues including melanocytes, except for testis. Because its expression was tested by reverse-transcription and PCR, the absence of a detectable product in normal tissues indicates a level of expression lower than 0.1% of that observed in tumor MZ2-MEL.

EXAMPLE 6

Expression of BAGE gene in tumor samples and cell lines was also determined. Six hundred samples of tumors of various histological origins were analyzed for BAGE expression. As shown in Table 2, below, BAGE gene is expressed mainly in melanomas (22%), bladder carcinomas (15%), mammary carcinomas (10%) and head and neck squamous cell carcinomas (8%). A smaller proportion of positive samples was found in sarcomas (6%) and in non-small cell lung carcinomas (6%). No expression of BAGE was found in renal, colorectal and prostatic carcinomas, leukemias, or lymphomas. With very few exceptions, tumor samples that expressed BAGE also expressed one of the MAGE genes discussed generally, supra.

TABLE 2

Expression of gene BAGE by tumor samples

| Histological type | Number of BAGE positive tumors* |  |
|---|---|---|
| Melanomas | 40/178 | |
| primary lesions | | 3/38 |
| metastatic lesions | | 37/140 |
| Bladder carcinomas | 9/62 | |
| superficial tumors | | 0/32 |
| infiltrating tumors | | 9/30 |
| Mammary carcinomas | 8/79 | |
| Head and Neck squamous cell carcinomas | 4/53 | |
| Lung carcinomas NSCLC° | 5/64 | |

TABLE 2-continued

Expression of gene BAGE by tumor samples

| Histological type | Number of BAGE positive tumors* |
|---|---|
| Sarcomas | 1/18 |
| Renal sarcomas | 0/50 |
| Colorectal carcinomas | 0/42 |
| Prostatic carcinomas | 0/22 |
| Leukemias and lymphomas | 0/22 |

*Expression of gene BAGE was tested by RT-PCR amplification of total RNA with the primers shown on FIG. 4.
°NSCLC = non small cell lung carcinomas BAGE was more frequently expressed in metastatic lesions of melanomas (26%) than in primary lesions (8%). In transitional-cell carcinomas of the urinary bladder, 30 of invasive tumors expressed BAGE, while no expression was observed in superficial tumors. BAGE was expressed in a higher proportion of tumor cell lines than of tumor samples: 32/60 melanoma (53%) and 3/15 colorectal carcinoma cell lines (20%) were positive. This has also been observed with MAGE genes, and may be due to the fact that tumor cell lines are more readily derived from metastatic tumors.

EXAMPLE 7

HLA-Cw*1601, the presenting molecule of BAGE antigen, cannot be identified in serological assays, as useful antibodies are not available. However, its expression can be tested by reverse transcription and nested PCR. Approximately 7% (7/99) of Caucasian individuals were found to express this HLA allele (van der Bruggen et al., supra). The concentration of HLA-C molecules on the cell surface has been reported to be about tenfold lower than that of HLA-A and B, possibly because of less efficient binding to β2-microglobulin (Neefjes et al., Eur. J. Immunol., 18:801–810 (1988)). Nevertheless, it has ben determined that BAGE codes for a peptide recognized on a HLA-C molecule, suggesting that HLA-C molecules also play a significant role in the presentation of antigens to CTL.

EXAMPLE 8

A Southern blot with DNA extracted from blood lymphocytes of patient MZ2 and from the melanoma cell line MZ2-MEL.3.0 was prepared. In order to perform Southern blot analysis, DNA from melanoma cell line MZ2-MEL.3.0, PBLs of patient MZ2 and mouse cell line P1.HTR were digested with EcoRI or HindIII. DNA capillary transfer was done by alkaline blotting on a Zeta-Probe® membrane (Bio-Rad). Following transfer, the membrane was rinsed in 2×SSC, baked for 1 hour at 80° C. and pretreated for 30 minutes at 60° C. in 6×SSC, 10×Denhardt's solution. The membrane was then hybridized for 18 hours at 65° C. in 3.5×SSC, 1×Denhardt's solution, 25 mM $NaH_2PO_4$ pH 7.0, 0.5% SDS, 2 mM EDTA, 100 μg/ml of herring sperm DNA, and $2 \times 10^6$ cpm/ml of a 121 bp $^{32}$P-labelled probe (nucleotides 211 to 331 of SEQ ID NO: 1) produced by PCR. The membrane was then washed at 65° C. for 2×15 minutes in 2×SSC, 0.5% SDS, then for 15 minutes in 0.2×SSC, 0.1% SDS, and autoradiographed for 10 days.

Figure 5:
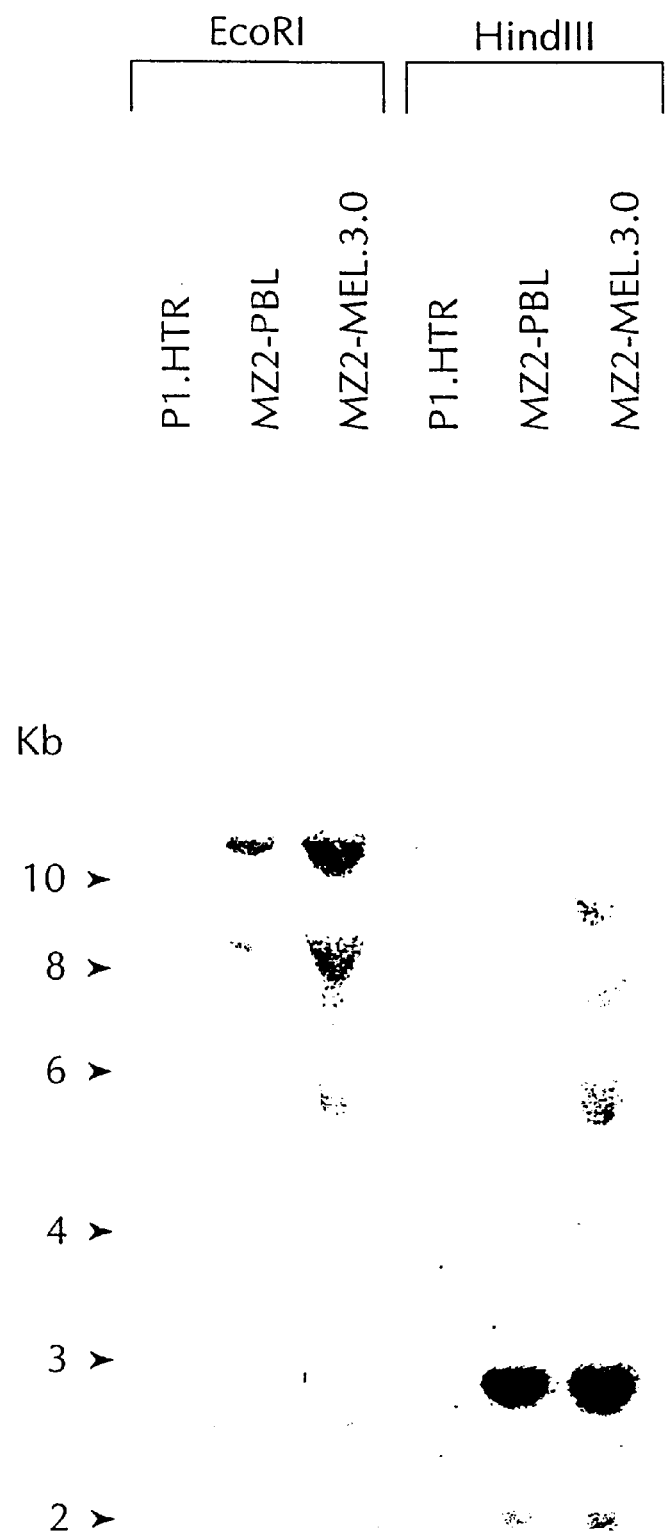
FIG. 5 represents Southern blots of -DNA extracted from melanoma cell line MZ2-MEL.3.0, blood lymphocytes from patient MZ2 and mouse cell line P1.HTR.

When this blot was hybridized with, the 121 bp probe described supra, four bands were observed in lanes containing DNA digested with EcoRI and 6 bands after HindIII digestion (FIG. 5). Considering the small size of the probe and considering the absence of EcoRI and HindIII restriction sites in the coding sequence, these results indicate that BAGE belongs to a family of several related genes.

EXAMPLE 9

A Northern blot prepared with poly-A+RNA of subline MZ2-MEL.43 was hybridized with a 286 bp BAGE probe including nucleotides 100 to 385 of SEQ ID NO: 1. To perform Northern blot analysis, poly-A+ RNA from MZ2-MEL.43 was prepared using mRNA extraction kit. Total RNA from mouse kidney tissue was extracted by the guanidine-isothiocyanate procedure as described by Davis et al., supra. Poly-A+ RNA was purified from total RNA on an oligo-dT column. For the Northern blot analysis, 5 µg of poly-A+ RNA from subline MZ2-MEL.43 and 5 µg of poly-A+ RNA from mouse kidney cells were fractionated on a 1% agarose gel containing 0.66 M formaldehyde and transferred on a membrane in 10×SSC.

The membrane was pre-hybridized for 15 minutes at 60° C. in 10% dextran sulfate, 1% SDS and 1 M NaCl and hybridized overnight at 60° C. in the same solution with $2 \times 10^6$ cpm/ml of the 286 bp $^{32}$P-labelled probe. The membrane was washed at room temperature in 0.2×SSC for 10 minutes and then 2×20 minutes at 60° C. in 0.2×SSC supplemented with 0.1% SDS, and autoradiographed for 15 hours. Control hybridization was performed on the same membrane with a mouse β-actin probe.

Figure 6:
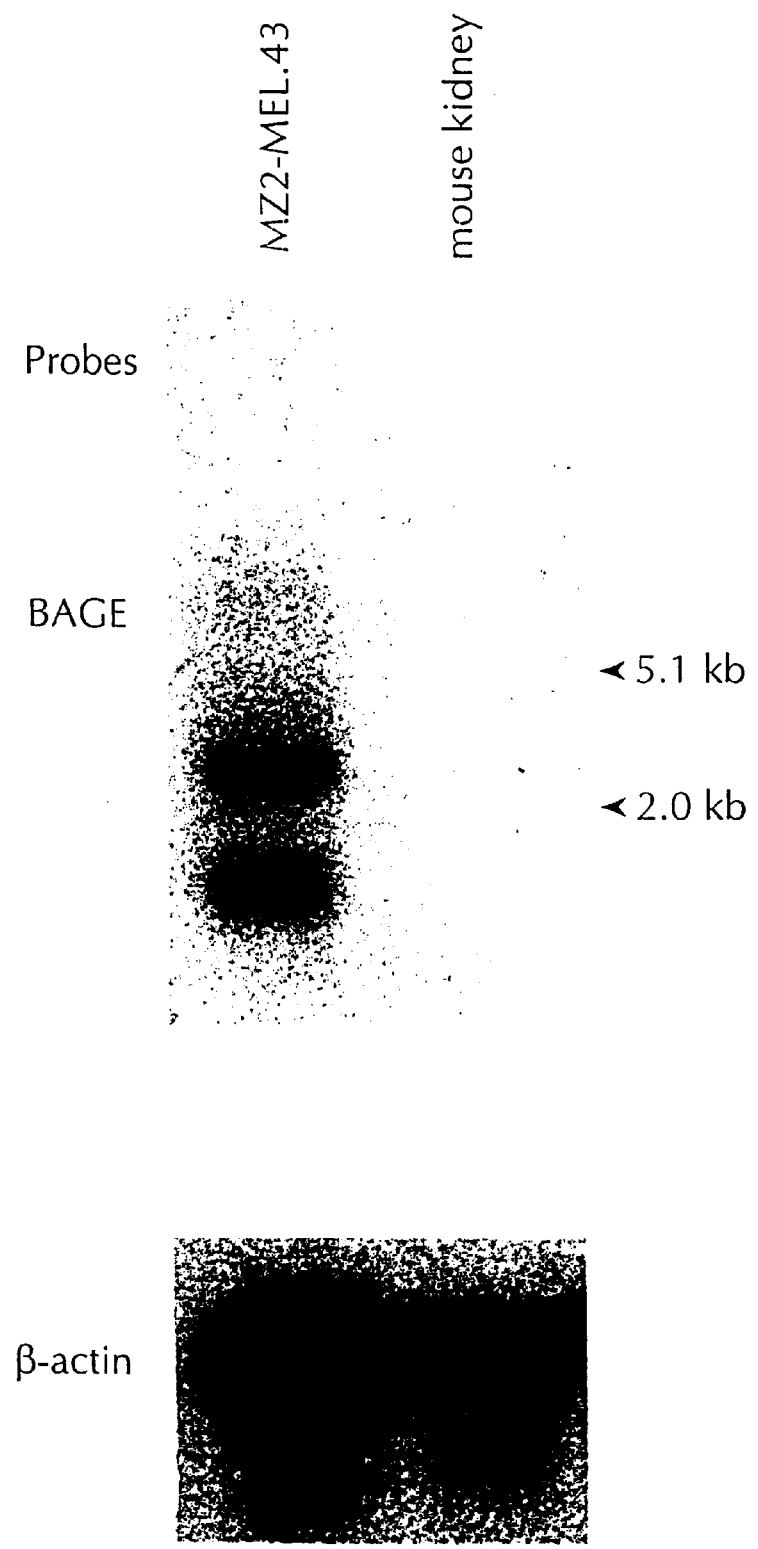
FIG. 6 represents Northern blot analysis of the expression of BAGE in MZ2-MEL.43 cells.

FIG. 6 shows the results of this work. Each lane contained 5 µg of poly-A+ RNA from MZ2-MEL.43 cells. Control hybridization was performed on the same membrane with a β-actin probe. Two bands of approximately 1 and 2.4 kb were observed.

Thus far, two main classes of antigens recognized by autologous CTL have been found on human melanoma. The antigens of the first class are encoded by genes that are expressed very specifically in tumors. An antigen encoded by gene MAGE-1 was the first example (van der Bruggen et al., *Science*, 254:1643–1647 (1991)), followed by other antigens encoded by genes MAGE-1 and MAGE-3 (Gaugler et-al., *J. Exp. Med.*, 179:921–930 (1994); van der Bruggen et al., supra). A tumor rejection antigen observed on mouse mastocytoma P815 also resulted from the activation of a gene which is silent in all normal adult tissues with the exception of testis (Van den Eynde et al., *J. Exp. Med.*, 173:1373–1384 (1991)). The second class of antigens represents differentiation antigens encoded by genes that are expressed only in melanocytes and melanomas. Antigens encoded by tyrosinase were the first examples of this class (Brichard et al., *Annal. Biochem.*, 162:156–159 (1993); Robbins et al., *Cancer Res.*, 54:3124–3126 (1994); Wolfel et al., *Eur. J. Immunol.*, 24:759–764 (1994)), which also comprises antigens encoded by Melan-A/MART-1 (Coulie et al., *J. Exp. Med.*, 180:35–42 (1994); Kawakami et al., *Proc. Natl. Acad. Sci. USA*, 91:3515–3519 (1994)) and gp 100/pmel17 (Bakker et al., *J. Exp. Med.*, 179:1005–1009 (1994); Cox et al., *Science*, 264:716–719 (1994)).

The foregoing examples show the isolation of a nucleic acid molecule which codes for a tumor rejection antigen precursor. This "TRAP" coding molecule, however, is not homologous with any of the previously disclosed MAGE coding sequences described in the references set forth supra. Hence, one aspect of the invention is an isolated nucleic acid molecule which comprises the nucleotide sequence set forth in SEQ ID NO: 1. This sequence is not a MAGE coding sequence, as will be seen by comparing it to the sequence of any of the MAGE genes described in the references. Also a part of the invention are those nucleic acid sequences which also code for a non-MAGE tumor rejection antigen precursor but which hybridize to a nucleic acid molecule containing the described nucleotide sequence, under stringent conditions. The term "stringent conditions" as used herein refers to parameters with which the art is familiar. More specifically, stringent conditions, as used herein, refers to hybridization in 3.5×SSC, 1×Denhardt's solution, 25 mM sodium phosphate buffer (pH 7.0), 0.5% SDS, and 2 mM EDTA for 18 hours at 65° C. This is followed by four washes of the filter at 2×15 minutes in 2×SSC, 0.5% SDS and 1×15 minutes in 0.2×SSC, 0.1% SDS at 65° C. There are other conditions, reagents, and so forth which can be used, which result in the same degree of stringency. The skilled artisan will be familiar with such conditions, and thus they are not provided herein.

It will also be seen from the examples that the invention includes the use of the sequences in expression vectors, as well as in the transformation or transfection of host cells and cell lines, including prokaryotic cell strains (e.g. *E. coli*), and eukaryotic cells (e.g., CHO or COS cells). The expression vectors require that the sequence be operably linked to a promoter. The expression vector may also include a nucleic acid sequence coding for HLA-Cw*1601. Where the vector contains both coding sequences, it can be used to transfect a cell which does not normally express either one. The tumor rejection antigen precursor coding sequence may be used alone, when, for example, the host cell already expresses HLA-Cw*1601. of course, there is no limit on the particular host cell which can be used. As the vectors which contain the two coding sequence may be used in HLA-Cw*1601 presenting cells if desired, and the gene for tumor rejection antigen precursor can be used in host cells which do not express HLA-Cw*1601.

The invention also includes expression kits, which allow the artisan to prepare a desired expression vector or vectors. Such expression kits include at least separate portions of each of the previously discussed coding sequences. Other components may be added, as desired, as long as the previously mentioned sequences, which are required, are included.

To distinguish the nucleic acid molecules and the TRAPs of the invention from the previously described MAGE family, the invention shall be referred to as the BAGE family of genes and TRAPs. "BAGE" refers to the tumor rejection antigen precursors coded for by the previously described sequence. "BAGE coding molecule" and similar terms, are used to describe the nucleic acid molecules themselves.

Also a part of the invention are peptides, for example, the peptide of SEQ ID NO: 3, which can be used to identify those cells which present MHC molecule HLA-Cw*1601. Administration of the peptides, carrying a detectable signal, e.g., followed by the identification of cells to which the peptide has bound, is one way to accomplish this. Another way to accomplish this is the use of solid phase bound peptides, to which HLA-Cw*1601 presenting cells bind, thus removing them from the sample being assayed.

Additionally, the invention permits the artisan to diagnose a disorder characterized by expression of the TRAP. These methods involve determining expression of the TRAP gene, and/or TRAs derived therefrom, such as the TRA presented by HLA-Cw*1601. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred. An alternate method for determination is a TNF release assay, of the type described supra.

The isolation of the TRAP gene also makes it possible to isolate the TRAP molecule itself, especially TRAP molecules containing the amino acid sequence coded for by SEQ ID NO: 1. These isolated molecules when presented as the TRA, or as complexes of TRA and HLA, such as HLA-Cw*1601, may be combined with materials such as adjuvants to produce vaccines useful in treating disorders characterized by expression of the TRAP molecule. In addition, vaccines can be prepared from cells which present. the TRA/HLA complexes on their surface, such as non-proliferative cancer cells and non-proliferative transfectants. Immunization against both BAGE and MAGE antigens can be undertaken. In all cases where cells are used as a vaccine, these can be cells transfected with coding sequences for one or both of the components necessary to prove a CTL response, or can be cells which express both molecules without transfection. Further, the TRAP molecule, its associated TRAs, as well as complexes of TRA and HLA, may be used to produce antibodies, using standard techniques well known to those skilled in the art.

When "disorder" is used herein, it refers to any pathological condition where the tumor rejection antigen precursor is expressed. An example of such a disorder is cancer melanoma in particular.

Therapeutic approaches based upon the disclosure are premised on a response by a subject's immune system, leading to lysis of TRA presenting cells, such as HLA-Cw*1601. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein, are widely available, as are other suitable host cells.

To detail the therapeutic methodology, referred to as adoptive transfer (Greenberg, *J. Immunol.*, 136 (5): 1917 (1986); Reddel et al., *Science*, 257: 238 (Jul. 10, 1992); Lynch et al., *Eur. J. Immunol.*, 21: 1403–1410 (1991); Kast et al., *Cell*, 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing DNA of the pertinent sequences, in this case a BAGE sequence. Once cells presenting the relevant complex are identified via the foregoing screening methodology, they can be combined with a sample from a patient, where the sample contains CTLs. If the complex presenting cells is lysed by the mixed CTL sample, then it can be assumed that a BAGE derived, tumor rejection antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., *Proc. Natl. Acad. Sci. USA*, 88: 110–114 (1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, for example, a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-Cw*1601 presenting cells which present the HLA molecule of interest. The TRAP is processed to yield the peptide partner of the HLA molecule. while the TRA is presented without the need for further processing.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method for determining expression of a nucleic acid molecule which encodes a tumor rejection antigen precursor, the amino acid sequence of which is set forth at SEQ ID NO: 2, comprising contacting a sample with an oligonucleotide which hybridizes specifically, under stringent conditions to a nucleotide sequence which encodes SEQ ID NO: 2, and determining said hybridization as a determination of expression of said nucleic acid molecule.

2. The method of claim 1, wherein said nucleic acid molecule comprises the nucleotide sequence set forth in SEQ ID NO: 1.

3. The method of claim 1, wherein said method is a polymerase chain reaction or nucleic acid blot hybridization assay.

4. The method of claim 3, wherein said method is a polymerase chain reaction.

5. The method of claim 1, comprising contacting said sample with oligonucleotides SEQ ID NO: 6 and SEQ ID NO: 7.

6. The method of claim 1, wherein said stringent conditions comprise hybridization in 3.5×SSC, 1×Denhardt's solution, 35 mM sodium phosphate buffer (pH 7.0), 0.5% SDS, and 2 mM EDTA for 18 hours at 65° C., followed by four washes at 2×15 minutes in 2×SSC, 0.5% SDS, and 1×15 minutes in 0.2×SSC, 0.1% SDS at 65° C.

7. The method of claim 1, wherein said oligonucleotide consists of a nucleotide sequence set forth in SEQ ID NO: 1.

* * * * *